United States Patent [19]

Thottathil

[11] Patent Number: 4,670,193
[45] Date of Patent: Jun. 2, 1987

[54] PROCESS FOR PREPARING PHOSPHONIC ACIDS

[75] Inventor: John K. Thottathil, Trenton, N.J.

[73] Assignee: E. R. Squibb & Sons, Inc., Princeton, N.J.

[21] Appl. No.: 861,795

[22] Filed: May 12, 1986

[51] Int. Cl.$^4$ ............................ C07F 9/38; C07F 9/40
[52] U.S. Cl. ...................... 260/502.4 R; 260/502.5 D; 558/132
[58] Field of Search ................ 558/132; 260/502.4 R, 260/502.5 D, 502.4 F

[56] References Cited

U.S. PATENT DOCUMENTS 4,168,267 9/1979 Petrillo, Jr. ...................... 260/326.2
4,316,896 2/1982 Thorsett et al. ................... 424/200
4,452,790 6/1984 Karanewsky et al. ............. 424/200

OTHER PUBLICATIONS

Emeleus et al, "Jou. of the Chem. Soc.", (London) (1955) pp. 563–574.
Pelchowicz, J. Chem. Soc., 1961, 238, "Organic Phosphorus Compounds, Part I, The reaction of Dialkyl Methylphosphonates and Methylphosphonothionates with Inorganic Acid Chlorides".
Green et al, Chem. Soc. 1958, 3129, "The Preparation of Optically Active Phosphorus Compounds".
Baylis, et al., J. Chem. Soc. Perkin Trans. 1, 2845 (1984) "1-Aminoalkylphosphonous Acids, Part 1, Isosteres of the Protein Amino Acids".
Kosolapoff et al., "Organic Phosphonous Compounds", Wiley–Interscience, N.Y., 1972, vol. 4, pp. 288 and 294–295 and vol. 7, p. 11.
Mehrotra, Can. J. Chem., 63 663 (1985) "Kinetics and Mechanisms of Oxidations by Metal Ions, Part IV—Oxidation of Phenylphosphinic Acid by Aquavanadium (V) Ions".
Guichard, Chem. Bev., 32 1572 (1899).
Hatt, J. Chem. Soc., 776 (1933) "The Constitutions of Some Phosphorous Derivatives of Triphenylmethane".
Michaels, Liebigs Annalen der Chemie, 315 51 (1901).

Primary Examiner—Anton H. Sutto
Attorney, Agent, or Firm—Lawrence S. Levinson; Burton Rodney

[57] ABSTRACT

A process for preparing phosphonic acids of the structure

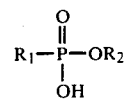

wherein $R_1$ is lower alkyl, aryl, cycloalkyl or arylalkyl, and $R_2$ is H, benzyl or

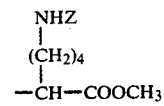

by oxidizing the corresponding phosphonous acid

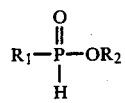

employing as the oxidizing agent potassium permanganate or sodium periodate.

11 Claims, No Drawings

PROCESS FOR PREPARING PHOSPHONIC ACIDS

FIELD OF THE INVENTION

The present invention relates to a process for preparing phosphonic acids which are useful in preparing angiotensin converting enzyme inhibitors used in treating hypertension as disclosed in U.S. Pat. No. 4,452,790.

BACKGROUND OF THE INVENTION

Phosphonic acids and their derivatives have become increasingly important in recent years due to their useful biological properties, such as their ability to lower blood pressure due to their angiotensin converting enzyme inhibition activity, such as disclosed in U.S. Pat. No. 4,316,896 to Thorsett, et al. and U.S. Pat. Nos. 4,168,267 to Petrillo and 4,452,790 to Karanewsky, et al.

The Arbuzov reaction of trialkylphosphites with suitable alkylating agents is a commonly used method for the preparation of phosphonic acid esters but it often requires high temperatures, neat reaction mixtures and other strong impractical conditions. Additionally, complex product mixtures are common due to competitive alkylation by alkyl halide side products generated in the reaction.

Z. Pelchowicz, J. Chem. Soc. 1961, 238 discloses the preparation of phosphonic acid esters by base catalyzed alkylation or base catalyzed Michael addition each of which frequently requires strongly alkaline conditions.

M. Green and R. F. Hudson, J. Chem. Soc. 1958, 3129 disclose the free radical addition of dialkylphosphites and derviatives which usually requires high reaction temperatures and pressures, while only affording moderate to low yields and mixtures of products.

The oxidation of phosphonous acids or its esters to phosphonic acids or its esters often requires strong, poisonous, expensive and gaseous reagents, namely, mercuric salts, periodates, nitrogen oxide gases and the like. E. K. Baylis, C. D. Campbell and J. G. Dingwall, J. Chem. Soc. Perkin Trans. 1, 2845 (1984), G. M. Kosolapoff and L.Maier, "Organic Phosphonous Compounds, Wiley-Interscience, N.Y. 1972, Vol. 4, pages 288 and 294–295 and Vol. 7, page 11, R. N. Mehrotra, Can. J. Chem., 63, 663 (1985); C. F. Guichard, Chem. Bev., 32 1572 (1899).

The oxidation of triphenylmethyl, phosphonous acid and dibenzyl phosphonous acids to the corresponding phosphonic acids is mentioned by H.K. Hatt, J. Chem. Soc. 776 (193) and A. Michaels, Liebigs Ann. Chem., 315 51 (1901).

Thus, a mild efficient inexpensive method for preparing phosphonic acids which may be used in making phosphonyloxyacylamino acid angiotensin converting enzyme inhibitors would be a most welcomed addition to the art.

Description of the Invention

In accordance with the present invention, convenient mild rapid and efficient process is provided for directly preparing phosphonic acids from corresponding phosphonous acids according to the following reaction:

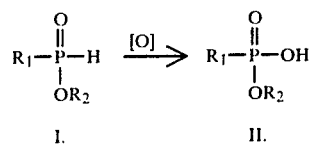

In carrying out the above reaction, phosphonous acid I is oxidized employing an oxidizing agent such as potassium permanganate, or sodium periodate, preferably potassium permanganate, in the presence of water, a solvent such as acetone, tetrahydrofuran or dioxane and a strong base such as an alkali metal hydroxide including sodium hydroxide, potassium hydroxide or lithium hydroxide, to form phosphonic acid II, in excellent yields, wherein $R_1$ is lower alkyl, aryl, cycloalkyl or arylalkyl, with arylalkyl being

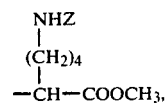

preferred, and $R_2$ is H, benzyl or

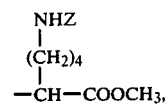

with H being preferred.

The phosphonous acid I will be dissolved in a suitable solvent as described above, preferably acetone and water. Aqueous base is added to achieve a desired pH of within the range of from about 4 to about 8.

A solution of the oxidizing agent in water is slowly added to a stirred solution of the phosphonous acid. The reaction mixture is then acidified with strong acid such as concentrated hydrochloric acid, sulfuric acid, or nitric acid to a pH of within the range of from about 4 to about 0.5 and base such as sodium bisulfite is added to precipitate out the phosphonic acid.

The oxidation of the phosphonous acid is carried out at a temperature within range of from about 0 to about 40° C. and preferably from about 15 to about 25° C. The reaction is slow at 0° C. but is instantaneous at from about 20 to about 25° C.

In general, the oxidizing agent will be employed in a molar ratio to phosphonous acid I of within the range of from about 0.25:1 to about 2:1, and preferably from about 0.5:1 to about 1:1.

The term "aryl," as used throughout the specification, either by itself or as part of a larger group, refers to phenyl or phenyl substituted with halogen, alkyl, alkoxy, alkylthio, hydroxy, alkanoyl, nitro, amino, dialkylamino or a trifluoromethyl group. Phenyl and monosubstituted phenyl are preferred and phenyl is the most preferred.

The term "alkyl" or "lower alkyl," as used throughout the specification, either by itself or as part of a larger group, refers to straight or branched chain groups having 1 to 10 carbon atoms in the normal chain which may include an aryl, cycloalkyl or halo substituent or amino substituent of the structure

wherein R₃ and R₄ may be the same or different and can be H, lower alkyl, arylalkyl, aryl, t-butyloxycarbonyl, benzyloxycarbonyl (also referred to as "Z"), benzhydryl or trityl. Alkyl groups having 1 to 4 carbon atoms are preferred.

The term "cycloalkyl," as used throughout the specification, either by itself or as part of a larger group, refers to group having 3 to 7 carbon atoms, such as cyclopropyl, cyclobutyl, cyclopentyl, cyclohexyl or cycloheptyl.

The term "arylalkyl" or "cycloalkylalkyl," as used throughout the specification, either by itself or as part of a larger group, refers to an "alkyl" group as defined above containing an "aryl" or "cycloalkyl" substituent.

The term "halo" or "halogen" as used throughout the specification either by itself or as part of a larger group, refers to Cl, Br, F, I or CF₃.

Examples of phosphonous acids I useful as starting materials in carrying out the present invention include, but are not limited to

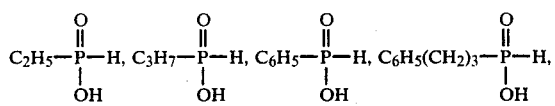

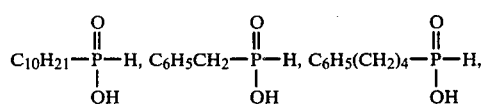

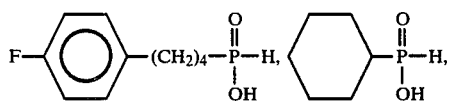

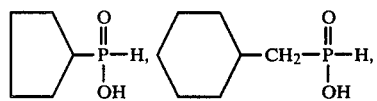

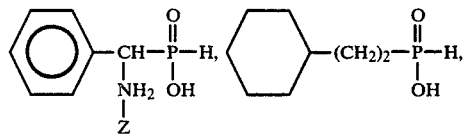

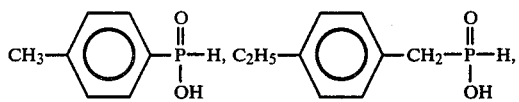

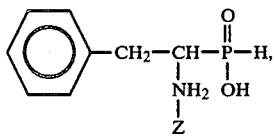

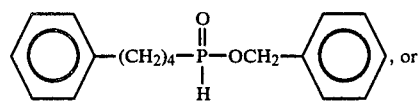

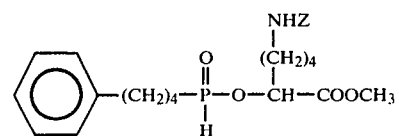

with

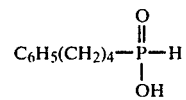

being preferred.

The phosphonous acids I are conventional compounds and may be prepared as described by E. E. Nifantev and M. P. Koroteev, J, Gen. Chem. (USSR), 37, 1293 (1967).

The following examples are illustrative and represent preferred embodiments of the invention. Temperatures are given in degrees centigrade. AG-50W-X8 refers to a cross-linked polystyrenedivinylbenzene sulfonic acid cation exchange resin. HP-20 refers to a porous cross-linked polystyrenedivinyl benzene polymer resin.

EXAMPLE 1 p-Fluorophenylbuty phosphonic acid

To a solution of p-fluorophenylbutyl phosponous acid (1 g, 0.0046 mole) in acetone (10 ml) and water (10 ml) was added a solution of sodium hydroxide (0.185 g, 0.0046 mole) in water (5 ml) until a pH of 7 was reached. A solution of KMnO₄ (0.44 gm, 0.0028 mole) in water (50 ml) was added slowly to the vigorously stirred solution of phosphonous acid at 20-25° C. After the addition (20 min), the reaction mixture was stirred for 10 min at ambient temperature and acidified with concentrated HCl acid until a pH 1 was reached. Saturated sodium bisulphite solution was added to the reaction mixture thereby resulting in formation of a cloudy white precipitate.

The precipitate was then crystallized from ethyl acetate/hexane to yield 0.92 gm., 86% yield, m.p. 115°-117° C.

Anal Calcd for $C_{10}H_{14}PO_3F$; C, 51.73; H; 6.08; F, 8.18; P, 13.34; Found: C, 51.75; H, 5.93; F, 8.0; P, 13.0.

EXAMPLE 2

1-(Benzyloxycarbonylamino)-2-phenylethyl-phosphonic acid

To a solution of 1-benzyloxycarbonylamino2-phenylethyl phosphonous acid (0.5 g, 0.0016 mole) in acetone (20 ml) and water (10 ml) was added a 10% solution of sodium hydroxide in water until a pH of about 7 was reached. A solution of KMnO₄ (0.14 g, 0.00086 mole, 0.55 equiv.) in water (10 ml) was added slowly to the vigorously stirred solution of phosphonous acid at 20-25° C. After the addition (5 minutes), the reaction mixture was stirred for 5 minutes at ambient temperature and acidified with concentrated HCl acid until a pH of 1 was reached. Saturated sodium bisulfite solution was added to the reaction mixture thereby resulting in formation of a white precipitate.

The precipitate was then crystallized from ethyl acetate/hexane to yield 0.41 gm, 78% yield, 155–157° C.

Anal Cald for $C_{16}H_{18}O_5PN$: C, 57.31; H, 5.41; P, 9.25; N, 4.18. Found: C, 57.06; H, 5.32; P, 8.9; N, 4.02.

EXAMPLE 3

Benzyloxycarbony amino (phenyl) methyl phosphonic acid

To a solution of (benzyloxycarbonyl) amino (phenyl) methyl phosphonous acid (1.35 g, 4.42 mmole) in acetone (10 ml) and water (10 ml) was added a solution of sodium hydroxide (0.176 g, 4.42 mmole) in water (10 ml) until a pH of about 7 was reached. A solution of $KMnO_4$ (0.419 g, 2.3 mole) in water (10 ml) was added slowly to the vigorously stirred solution of phosphonous acid at 20–25° C. After the addition (5 minutes), the reaction mixture was stirred for 10 minutes at ambient temperature and acidified with concentrated HCl acid until a pH of 1 was reached. Saturated sodium bisulfite solution was added to the reaction mixture thereby resulting in formation of a precipitate.

The precipitate was then crystallized form ethyl acetate/hexane to yield 1.2 gm, 84% yield, m.p. 149°–158° C.

Anal Calcd (for 1-adamantanamine salt), 1.05 M of $H_2O$: C, 60.97; H, 7.39; N, 5.69; P. 6.29. Found: C, 60.97; H, 7.11; N, 5.46; P, 6.00.

EXAMPLE 4

Phenylphosphonic acid

To a solution of phenylphosphonous acid (1 g, 0.007 mole) in acetone (10 ml) and water (10 ml) was added a solution of sodium hydroxide (0.281 gm, 0.007 mole) in water (10 ml) until a pH of about 7 was reached. A solution of $KMnO_4$ (0.663 g, 0.007 mole) in water (10 ml) was added slowly to the vigorously stirred solution of phosphonous acid at 20°–25° C. After the addition (5 minutes), the reaction mixture was stirred for 5 minutes at ambient temperature and acidified with concentrated HCl acid until a pH of 1 was reached. Saturated sodium bisulfite solution was added to the reaction mixture thereby resulting in formation of a precipitate.

The precipitate was then crystallized from ethyl acetate/hexane to yield 0.54 g, 47% yield, m.p. 153°–154° C.

Anal Calcd for $C_6H_7PO_3$: C, 45.58; H, 4.06; P, 19.59. Found: C, 45.77; H, 4.16; P, 19.50.

EXAMPLE 5 n-Decylphosphonic acid

To a solution of n-decylphosphonous acid (1 g, 0.0048 mole) in acetone (10 ml) and water (10 ml) was added a solution of sodium hydroxide (0.19 gm, 0.0047 mole) in water (5 ml) until a pH of about 7 was reached. A solution of $KMnO_4$ (0.46 gm, 0.0029 mole) in water (5 ml) was added solwly to the vigorously stirred solution of phosphonous acid at 20–25° C. After the addition (5 minutes), the reaction mixture was stirred for minutes at ambient temperature and acidified with concentrated HCl acid until a pH of 1 was reached. Saturated sodium bisulfite solution was added to the reaction mixture thereby resulting in formation of a precipitate.

The precipitate was then crystallized from ethyl acetate/hexane to yield 0.53 gm, 49% yield, m.p. 101° C.

Anal Calcd for $C_{10}H_{23}O_3P$: C, 54.03; H, 10.43; P, 13.93. Found: C, 53.76; H, 10.41; P, 14.0.

EXAMPLE 6

(Benzyloxycarbonyl)amino(n-butyl)methyl phosphonic acid

To a solution of (benzyloxycarbonyl)amino(n-butyl)-methyl phosphonous acid (0.3 g, 0.0011 mole) in acetone (10 ml) and water (10 ml) was added a solution of sodium hydroxide (0.043 g, 0.0012 mole) in water (10 ml) until a pH of about 7 was reached. A solution of $KMnO_4$ (0.04 g, 0.001 mole) in water (10 ml) was added slowly to the vigorously stirred solution of phosphonous acid at 20°–25° C. After the addition (5 minutes), the reaction mixture was stirred for 5 minutes at ambient temperature and acidified with concentrated HCl acid until a pH of 1 was reached. Saturated sodium bisulfite solution was added to the reaction mixture thereby resulting in formulation of a white precipitate.

The precipitate was then crystallized from ethyl acetate/hexane to yield 0.17 g, 53% yield, m.p. 102°–104° C.

Anal Cald. for $C_{13}H_{20}O_5NP$: C, 49.74, H, 6.87; N, 4.46; P, 9.87. Found: C, 49.81; H, 6.69, N, 4.42, P, 9.7.

EXAMPLE 7

4-Methylpentyl phosphonic acid

To a solution of 4-methylpentyl phosphonous acid (0.64 g, 4.2 mmole) in acetone (10 ml) and water (10 ml) was added a solution of sodium hydroxide (0.208 g, 0.005 mole) in water (10 ml) until a pH of about 7 was reached. A solution of $KMnO_4$ (0.399 g, 2.52 mmole) in water (10 ml) was added slowly to the vigorously stirred solution of phosphonous acid at 20°–25° C. After the addition (5 minutes), the reaction mixture was stirred for 5 minutes at ambient temperature and acidified with concentrated HCl acid until a pH of 1 was reached. Saturated sodium bisulfite solution was added to the reaction mixture thereby resulting in formation of a precipitate.

The precipitate was then crystallized form ethyl acetate/hexane to yield 0.444 g, 42% yield, m.p. 129°–130° C.

Anal Cald for $C_6H_{15}O_3P$: C, 41.80; H, 9.18; P, 17.96. Found: C, 41.80; H, 9.10; P, 17.8.

EXAMPLE 8

3-Phenylpropyl phosphonic acid

To a solution of 3-phenylpropyl phosphonous acid (0.92 g, 0.005 mole) in acetone (10 ml) and water (10 ml) was added a solution of sodium hydroxide (0.2 g, 0.005 mole) in water (10 ml) until a pH of about 7 was reached. A solution of $KMnO_4$ (0.474 g, 0.003 mole) in water (10 ml) was added slowly to the vigorously stirred solution of phosphonous acid at 20°–25° C. After the addition (5 minutes), the reaction mixture was stirred for 5 minutes at ambient temperature and acidified with concentrated HCl acid until a pH of 1 was reached. Saturated sodium bisulfite solution was added to the reaction mixture thereby resulting in formation of a precipitate.

The precipitate was then crystallized from ethyl acetate/hexane to yield 0.58 g, 58% yield, m.p. 117°–119° C.

Anal Cald for $C_9H_{13}O_3P$: C, 54.00; H, 6.54; P, 15.47. Found: C, 53.74; H, 6.57; P, 15.3.

EXAMPLE 9 n-Butyl phosphonic acid

To a solution of n-butyl phosphonous acid (1 g, 0.0082 mole) in acetone (10 ml) and water (10 ml) was added a solution of sodium hydroxide (0.327 g, 0.0082 mole) in water (10 ml) until a pH of about 7 was reached. A solution of KMnO4 (0.776 g, 0.0049 mole, 0.6 equiv.) in water (8 ml) was added slowly to the vigorously stirred solution of phosphonous acid at 20°–25° C. After the addition (5 minutes), the reaction mixture was stirred for 5 minutes at ambient temperature and acidified with concentrated HCl acid until a pH of 1 was reched. Saturated sodium bisulfite solution was added to the reaction mixture thereby resulting in formation of a precipitate.

The precipitate was then crystallized from ethyl acetate/hexane to yield 0.58 g, 51% yield, m.p. 100°–101° C.

Anal Cald for $C_4H_{11}O_3P$: C, 34.10; H, 8.09, P, 21.98. Found: C, 34.10; H, 7.77; P, 21.9.

EXAMPLE 10

4-Phenylbutylphosphonic acid-mono-benzyl ester

To a solution of 4-phenylbutylphosphonous acid benzyl ester (1.0 gm, 0.0035 moles) in 10 ml acetone and 5 ml water was added a solution of potassium permanganate (0.16 gm, 0.0021 moles) in 5 ml water at 20° C. After the addition (2 minutes), the reaction mixture was stirred at 20° C. for 5 minutes and acidified to pH 1 using concentrated HCl acid. Saturated sodium bisulphite solution was added to the reaction mixture to get a cloudy white solution, which on extraction with ethyl acetate followed by solvent evaporation produced the title compound as a pale yellow oil in 87% (0.92 gm) yield.

Anal Calcd for $C_{17}H_{21}O_2P$, 0.31M.H O: C., 66.12; H, 6.73; P, 10.03. Found: C, 66.12; H, 7.0; P, 10.2.

EXAMPLE 11

Methyl-(S)-[6-benzyloxycarbonylamino-2-[hydroxy(4-phenylbutyl)phosphinyl]oxy]hexanoate To a solution of methyl-(S)-[6-benzyloxycarbonylamino-2-[hydro(4-phenylbutyl)phosphinyl]-oxy]-hexanoate (25.74 gm, 0.054 mole) in acetone (200ml) was added a solution of potassium permanganate (5.12 gm, 0.032 mole) in water (100 ml) at 20° C. After the addition (20 minutes) the reaction mixture was stirred for 5 minutes and acidified to pH=1 using concentrated HCl acid. Saturated sodium bisulphite solution was added to the reaction mixture to obtain a white cloudy solution and most of the acetone was removed on rotovap. The residue was extracted with ethyl acetate (3×100 ml) and on solvent evaporation the title compound was obtained in 95% (25.18 gm) yield as a single spot material. TLC; $CH_2Cl_2$-HOAc-MeOH; 17:1.5:1.5, $R_f$=0.61. The corresponding diacid obtained on methyl ester hydrolysis formed a crystalline solid derivative with dicyclohexylamine, m.p. 107°–112° C.

EXAMPLE 12

4-Phenylbutylphosphonic acid

4-Phenylbutylphosphonous acid (47.19 gm, 0.238 mole) was dissolved in acetone (250 ml) and diluted with water (50 ml). Sodium hydroxide solution (9.5 gm, 0.238 mole) in water (50 ml) was added to it to get pH=7.0. The reaction mixture was cooled to 20° C. and potassium permanganate solution (22.5 gm, 0.142 mole) in water (250 ml) was added to it with stirring and maintaining the temperature around 20°-2° C. After the addition (15 minutes), the reaction mixture was stirred for 15 minutes at room temperature, acidified to pH 0 using concentrated HCl acid and saturated sodium bisulphite solution was added to it to get a white cloudy precipitate. Standard extractive workup using ethyl acetate followed by crystallization from ethyl acetate/hexane produced the title compound in 87% (44.16 gm) yield, m.p. 93° C.

TLC: $R_f$=0.25 ($C_2Cl_2$:MeOH:HOAc; 17:1.5:1.5; silica gel iodine and UV visualization).

Anal Calcd for $C_{10}H_{15}O_3P$: C, 56.07; H, 7.02; P, 14.46. Found: C,56.05; H, 7.06; P, 14.50.

[$^{13}C$ NMR spectral data]

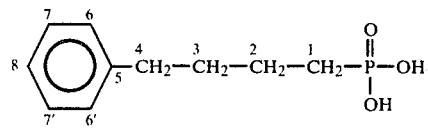

| Carbon | PPm |
| --- | --- |
| 1 | 25.27 (d, 145.50 Hz) |
| 2 | 32.15 (d, 16.60 Hz) |
| 3 | 21.92 (d, 4.0 Hz) |
| 4 | 35.44 |
| 5 | 142.01 |
| 7,6,8 | 128.44 |
| 7',6' | 125.90 |

What is claimed is:

1. A process for preparing phosphonic acids of the structure

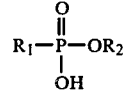

wherein $R_1$ is lower alkyl, aryl, or cycloalkyl, and $R_2$ is H, benzyl or

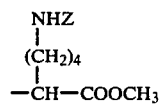

wherein Z is benzyloxycarbonyl, which comprises directly oxidizing a phosphonous acid of the structure

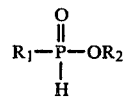

employing as an oxidizing agent potassium permanganate in the presence of a strong base, to form the corresponding phosphonic acid, and recovering said phosphonic acid.

2. The process as defined in claim 1 wherein the phosphonous acid is oxidized in the presence of a solvent therefor and said strong base is an alkali metal base.

3. The process as defined in claim 1 wherein the oxidizing agent is employed in a molar ratio to phosphonous acid of within the range of from about 0.25:1 to about 2:1.

4. The process as defined in claim 1 wherein the oxidation is carried out at a temperature within the range of from about 0 to about 40° C.

5. The process as defined in claim 1 wherein the $R_1$ group in the starting phosphonous acid is phenylalkyl, aryl or lower alkyl and $R_2$ is H.

6. The process as defined in claim 5 wherein $R_1$ is

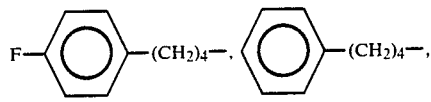

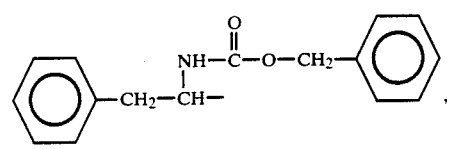

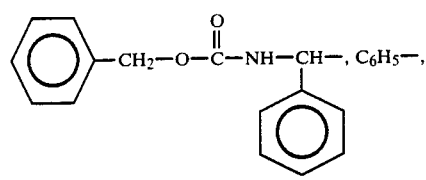

-continued

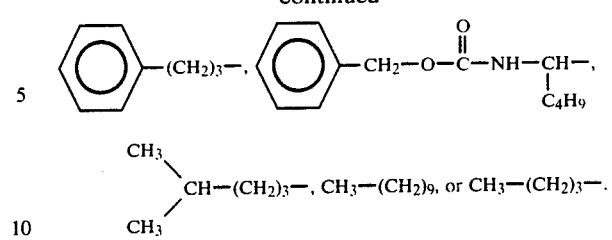

7. The process as defined in claim 2 wherein the phosphonous acid is initially dissolved in acetone and water and the base employed is NaOH and water.

8. The process as defined in claim 1 wherein the oxidation is carried at a pH within the range of from about 4 to about 8.

9. The process as defined in claim 8 wherein the oxidation is carried out at neutral pH.

10. The process as defined in claim 4 wherein the oxidation is carried out at a temperature of from about 20 to about 25° C.

11. The process as defined in claim 6 wherein $R_1$ is

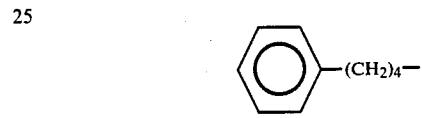

and $R_2$ is H.

* * * * *